United States Patent [19]

Kuo

[11] Patent Number: 5,221,748

[45] Date of Patent: Jun. 22, 1993

[54] PROCESS FOR THE PRODUCTION OF 2,3-DICHLORO-5-ACETYLPYRIDINE

[75] Inventor: David L. Kuo, Brig, Switzerland

[73] Assignee: Lonza Ltd., Gampel/Valais, Switzerland

[21] Appl. No.: 668,116

[22] Filed: Mar. 12, 1991

[30] Foreign Application Priority Data

Mar. 14, 1990 [CH] Switzerland ........................ 834/90

[51] Int. Cl.$^5$ .......................................... C07D 211/70
[52] U.S. Cl. .................................................... 546/314
[58] Field of Search ................ 546/315, 314, 296, 298

[56] References Cited

U.S. PATENT DOCUMENTS 4,358,455 11/1982 Atkinson et al. .................... 424/263
4,927,938 5/1990 Lindel et al. ......................... 546/315
5,051,513 4/1991 Jelich ................................... 546/315

FOREIGN PATENT DOCUMENTS 0299277 6/1988 European Pat. Off. .
0341478 4/1989 European Pat. Off. .

OTHER PUBLICATIONS

Fieser, Louis F., et al., "Reagents For Organic Synthesis", John Wiley and Sons, Inc., vol. 1, (1967), pp. 167–169.

*Primary Examiner*—C. Warren Ivy
*Assistant Examiner*—Raymond Covington
*Attorney, Agent, or Firm*—Fisher, Christen & Sabol

[57] ABSTRACT

Process for the production of 2,3-dichloro-5-acetylpyridine by reaction of a 5,6-dichloronicotinic acid halide with a methyl magnesium halide in an inert organic diluent. The reaction is performed in the presence of a Cu/Cu halide as the catalyst.

6 Claims, No Drawings

PROCESS FOR THE PRODUCTION OF 2,3-DICHLORO-5-ACETYLPYRIDINE

BACKGROUND OF THE INVENTION

1. Field Of The Invention

The invention relates to a process for the production of 2,3-dichloro-5-acetylpyridine.

2. Background Art

According to European Published Patent Application No. 0341478, 2,3-dichloro-5-acetylpyridine is produced from 5,6-dichloronicotinic acid halides with methyl magnesium halide in the presence of iron catalysts, such as, iron (II) chloride or tris-(2,4-pentanedionato) iron. In this known method, the yields, relative to 5,6-dichloronicotinic acid halide, are about 50 percent.

BROAD DESCRIPTION OF THE INVENTION

The main object of the invention is to provide a process that achieves substantially higher yields than the above-described prior art process. Other objects and advantages of the invention are set out herein or are obvious herefrom. The objects and advantages of the invention are achieved by the invention process.

The invention involves a process for the production of 2,3-dichloro-5-acetylpyridine by reacting of a 5,6-dichloronicotinic acid halide with a methyl magnesium halide in an inert organic diluent. The reaction is performed in the presence of a Cu/Cu halide as the catalyst.

2,3-Dichloro-5-acetylpyridine is an intermediate product for the production of pyridylethanolamines, active ingredients for the promotion of the performance of animals.

DETAILED DESCRIPTION OF THE INVENTION

Preferably the reaction is started from 5,6dichloronicotinic acid chloride, which is reacted with magnesium chloride in the presence of a catalytic amount of Cu/CuCl. Of course, other 5,6-dichloronicotinic acid halides, such as, bromide or iodide, and other methyl magnesium halides, such as, methyl magnesium bromide, can be used.

In the reaction, 0.8 to 1.2 mol of the methyl magnesium halide and 1 to 10 mol percent of the catalyst are used per mol of the 5,6-dichloronicotinic acid halide.

The reaction is performed in the presence of an inert organic diluent, such as, an ether, e.g., diethyl ether, dibutyl ether and glycol dimethyl ether, dioxane, an aliphatic or aromatic hydrocarbon, e.g., pentane, hexane, heptane, cyclohexane, benzene, toluene and benzine, and petroleum either. Tetrahydrofuran is preferably used as the inert organic diluent. The reaction temperature is suitably at $-70°$ C. to $+30°$ C., preferably $-30°$ C. to $0°$ C. The working up of the reaction mixtures takes place as is customary with Grignard reactions.

EXAMPLE

Production of 2,3-dichloro-5-acetylpyridine 25.4 g (120.7 mmol) of 5,6-dichloronicotinic acid chloride, 79 mg (1.2 mmol) of copper powder and 119 mg (1.2 mmol) of copper (I) chloride were placed in a round-bottom flask. After expulsion of air by nitrogen, 200 ml of dry tetrahydrofuran was added and the mixture was cooled to $-30°$ C. A this temperature, 40 ml of a 3 molar solution of methyl magnesium chloride (120.4 mmol) in tetrahydrofuran was instilled in 1.5 hours. The reaction mixture was then stirred for 1 more hour and then quenched with 25 ml of a saturated common salt solution. After the usual working up (extraction with ethyl acetate), 22.4 g of crude product was obtained which, according to GC, exhibited a content of 96.3 percent of 2,3-dichloro-5-acetylpyridine and 3.5 percent of the corresponding carbinol. This corresponded to a 94 percent yield of 2,3-dichloro-5-acetylpyridine.

What is claimed is:

1. Process for the production of 2,3-dichloro-5-acetylpridine comprising reacting 5,6-dichloronicotinic acid chloride with methyl magnesium chloride in an inert organic diluent, the reaction being performed in the presence of Cu/CuCl as a catalyst, and 0.8 to 1.2 mol of the methyl magnesium chloride and 1 to 10 mol percent of the Cu/CuCl catalyst being used per mol of the 5,6-dichloronicotinic acid chloride.

2. Process according to claim 1 wherein the inert organic diluent is tetrahydrofuran.

3. Process according to claim 1 wherein the inert organic diluent is diethyl ether, dibutyl ether, glycol dimethyl ether, dioxane, pentane, hexane, heptane, cyclohexane, benzene, toluene, benzine or petroleum ether.

4. Process according to claim 1 wherein the inert diluent is an ether, an aliphatic hydrocarbon or an aromatic hydrocarbon.

5. Process according to claim 1 wherein the reaction is conducted at $-70°$ C. to $+30°$ C.

6. Process according to claim 1 wherein the reaction is conducted at $-30°$ C. to $0°$ C.

* * * * *